United States Patent [19]

Poshkus

[11] 4,277,402
[45] Jul. 7, 1981

[54] SYNTHESIS OF POLYFORMALS

[76] Inventor: Robert A. Frosch, Administrator of the National Aeronautics and Space Administration, with respect to an invention of Algirdas C. Poshkus, Lancaster, Pa.

[21] Appl. No.: 54,501

[22] Filed: Jul. 3, 1979

[51] Int. Cl.$^3$ .................... C07D 317/00; C07C 43/30
[52] U.S. Cl. .............................. 260/340.9 R; 568/445; 568/497
[58] Field of Search ................. 260/602, 340.7, 340.9; 568/445, 448, 449, 496, 497

[56] References Cited

U.S. PATENT DOCUMENTS

| | | | |
|---|---|---|---|
| 1,934,309 | 11/1933 | Hoover | 260/240.9 R |
| 2,915,530 | 12/1959 | Kray et al. | 260/340.7 |
| 3,621,034 | 11/1971 | Fruhstorfer et al. | 260/340.7 |
| 3,978,088 | 8/1976 | Renner et al. | 260/340.9 |
| 4,076,727 | 2/1978 | Zey et al. | 260/340.7 |

OTHER PUBLICATIONS

Walker, "Formaldehyde", ACS Monograph Series 3rd ed., Reinhold Pub. Vo 1964, p. 206.
Ness et al., "J. Amer. Chem. Soc.", vol. 65, p. 2215 + (1976).
Schultz, "Ber.", vol. 27, p. 1892 + (1894).
Tollens "Ann.", vol. 289, p. 20 (1896).

*Primary Examiner*—Werren B. Lone
*Attorney, Agent, or Firm*—Darrell G. Brekke; John R. Manning

[57] ABSTRACT

Formals of $CH_2OH(CHOH)_nCH_2OH$ polyols (n=2 to 4) are prepared in less than 15 minutes by heating to about 125° C., a mixture of e.g. sorbitol and paraformaldehyde in slight excess (5 to 10%), in the presence of e.g. sulfuric acid in catalytic quantities. Elution with methanol and filtration yield the pure solid cyclic triformal. The process can be carried in stages, using almost stoichiometric quantities of paraformaldehyde, but without any change in overall heating time.

7 Claims, No Drawings

SYNTHESIS OF POLYFORMALS

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; 42 U.S.C. 2457).

BACKGROUND OF THE INVENTION

1. Field of the Invention

The present invention relates to formals of polyhydroxy compounds and more particularly to an improved method of preparing them.

2. Description of the Prior Art

Formals of compounds having the formula $CH_2OH(CHOH)_nCH_2OH$ have been prepared by reaction with formaldehyde under acid conditions and, in many cases, are well characterized. The processes of the art, however, involve reaction times in the order of several hours or days, and isolation procedures which often are complex and time-consuming. For example, the triformals of mannitol and of sorbitol were prepared by Schultz and Tollens [Ber. 27, 1892 (1894) and Ann. 289, 20 (1896)] by heating the polyol with 40% formaldehyde and concentrated hydrochloric acid under a reflux condenser for $\frac{3}{4}$ to $1\frac{1}{2}$ hour, followed by filtration after several hours. No yields were given. Ness et al [J. Am. Chem. Soc. 65, 2215 (1943)], who obtained only a 40% yield of mannitol triformal by the Schultz and Tollens procedure, improved it by heating the mannitol, 10 g, with formalin, 17.5 g, and concentrated hydrochloric acid, 20 ml, at 50° C. for 5 days. After filtering off the triformal, more heating of the filtrate for 4 days at 50° C. brought the total yield to 93%. Ouchi and So [J. Macromol. Sci. Chem A 10, 1599 (1976)] substituted sulfuric acid for hydrochloric acid in preparing sorbitol triformal by the Ness et al method, but again, long reaction periods and large volumes of water were involved.

More recent efforts in the preparation of various acetals of pentaerythritol offer no clues on the possible improvement of the conventional preparations of polyol formals. Renner et al (U.S. Pat. No. 3,978,088), for instance, prepare diacetals with dimeric β-OH-pivaldehyde in hydrochloric acid by a 24 hour reaction. Fruhstorfer et al (U.S. Pat. No. 3,621,034), on the other hand, boil pentaerythritol with dodecylthiopropanal for $3\frac{1}{2}$ hours, while Kray et al (U.S. Pat. No. 2,915,530) obtain their diacetals with e.g. acrolein after a 4 hour reflux period in the presence of 0.1% phosphoric acid.

Finally, Zey et al (U.S. Pat. No. 4,076,727) still more recently disclosed the preparation of cyclic acetal from polyols, e.g. trimethylolpropane, and an aldehyde such as formaldehyde and butyraldehyde, by refluxing such compounds in, e.g. benzene for a period of at least 4 hours. The possibility of higher temperatures, i.e., up to 150° C., is mentioned, solvent permitting it is assumed. In any event, Zey et al appear to be committed to a conventional process to obtain the acetals that they need for the synthesis of acrylic esters.

In summary, the processes that have just been reviewed, as well as several other existing approaches, variously suffer from one or more of the following shortcomings, namely: long reaction times—hours or days; long cooling times; inferior yield of product; time-consuming procedures for isolation; use of solvents; high expenditure of energy; and inadaptability to continuous production.

In view of this situation, it is the principal object of this invention to provide a process which will be free of any and all of the art limitations just enumerated.

SUMMARY OF THE INVENTION

It has now been discovered that the formals of $CH_2OH(CHOH)_nCH_2OH$ polyols (n=2 to 4) can be prepared in good yield in less than 15 minutes, by heating rapidly to a temperature of about 125° C. a mixture of the polyol with a slight excess (5 to 10%) of paraformaldehyde in the presence of an acid catalyst such as sulfuric acid. Elution with e.g. methanol, and filtration leave the insoluble formals as pure white products. The formation of di- and triformals can be accomplished in stages, with attendant reduction of paraformaldehyde quantity to almost stoichiometric levels. The total heating time remains unchanged.

DETAILED DESCRIPTION OF THE INVENTION

To obtain the formals of polyhydroxy compounds of the formula $CH_2OH(CHOH)_nCH_2OH$, a powdered mixture of the compound selected and a slight excess of paraformaldehyde are typically heated together rapidly with stirring, in the presence of an acidic catalyst to a temperature of about 125° C. Total heating time lasts from about 5 to 15 minutes. During this period, the solids first turn into a paste at about 70° C., liquify at about 100° C., and are finally converted into a dry powder at a temperature between 115° and 125° C.

Catalytic quantities of an acidic compound, i.e. about 0.1 to 1.0 mole % must be present. Usable compounds for this purpose include hydrochloric acid, sulfuric acid, methanesulfonic acid, zinc chloride with hydrochloric acid, and the like. Since hydrochloric acid may produce some of the carcinogenic bis(chloromethyl)ether, other acids are preferred. When anhydrous acids or compounds are used, a small quantity of water, about 1% of the total weight of the reactants, is used to help convert the mixture into a paste for ease of stirring and better heat transfer. Aside from this convenience, however, water is not essential for good yield of product.

If the reaction is carried out in stages, the quantity of paraformaldehyde can be reduced to almost stoichiometric levels, i.e. less than 1% excess. The yield of polyformal is improved, but the total heating time remains virtually the same as in the one-stage approach. In the first stage, for instance, a hexitol is heated with two equivalents of paraformaldehyde to about 120° C. in 5 minutes, then cooled to about 75° C. A third equivalent of paraformaldehyde, with 1% excess, is added to the warm mixture and heating is continued at 115°–125° C. until a solid powder is obtained. This second operation takes about 5 minutes for a total heating time of ten minutes.

Whichever preparation is used, the resultant crude white powder is suspended in a small quantity of acetone or methanol and the thick paste is filtered, a surprising rapid process. The white powder remaining is quite pure and constitutes a yield of within the range of 80 to 90%. Methanol is preferred for this elution process in cases where further product recovery is to be attempted. In such instances, the filtrate and washings are concentrated, treated with more paraformaldehyde in the manner already described to bring the total yield to more than 95%.

The following examples will now illustrate the practice of the invention in operational detail. In all the preparations described, the reagents are of commercial quality and are employed as received, except for occasional powdering of solids, as necessary.

EXAMPLE 1

A mixture of 18.2 g of sorbitol, 9.5 g of paraformaldehyde, 0.5 g of zinc chloride, and 4 ml of concentrated hydrochloric acid was heated in 2 min to 90°–100° C. The thin slurry converted into a clear liquid and almost immediately into a paste with evolution of some formaldehyde vapors. Heating and stirring was continued at 110°–115° C. until the paste turned into a powder (about 8 min). The tan powder (21.8 g, mp 175°–183° C.) was cooled, stirred with 25 ml of acetone and the thick paste filtered. Filtration proceeded readily. The insoluble powder was washed with acetone (3×5 ml) and dried to give 16.7 g of a fine white powder, mp 214°–216° C. Evaporation of the combined filtrate and washings left 5.3 g of a viscous oil or paste; treatment with 1.5 g of paraformaldehyde and 1 ml of hydrochloric acid as before gave an additional crop of white powder (3.4 g, mp 214°–216° C.) for a combined yield of 95%. 1,3:2,4:5,6-Trimethylenesorbitol is reported to melt at 212°–216° C.

EXAMPLE 2

The procedure of Example 1 was repeated with 5 g of 40% sulfuric acid in lieu of the zinc chloride—hydrochloric acid catalyst. The crude product was washed with methanol rather than acetone. The purity and yield achieved were similar to those of Example 1.

EXAMPLE 3

A mixture of sorbitol, 9.1 g, paraformaldehyde, 3.1 g, and 25% sulfuric acid, 1.3 g, was heated in 1.5 min to 100°–105° C. and kept at this temperature to get a clear liquid. The temperature was raised to and kept at 110°–120° C. for 2.5 min. The liquid was cooled and paraformaldehyde, 1.6 g, was added to the soft paste at 75° C. The temperature was raised to and kept at 105°–110° C. for 2 min, during which time the slurry cleared and solidified to a paste. Heating was continued at 110°–120° C. for 3 min to obtain 10.9 g of white powder, mp 178°–185° C. When the product was cold, 20 ml of methanol was added, the slurry stirred, and then the thick paste filtered and washed with 3×5 ml methanol to leave a white powder (9.1 g, mp 213°–215° C.). Concentration of the colorless filtrate and washings left 1.5 g of oily crystals.

EXAMPLE 4

The procedure of Example 1 was repeated with mannitol, 18.2 g, instead of sorbitol. A 21.7 g yield of crude white powder (mp 183°–197° C.) was obtained. The acetone-insoluble white powder (15.4 g) melted at 229°–230° C. A second crop was obtained from the filtrate and the washings on treatment with paraformaldehyde and hydrochloric acid: 5.0 g, mp 228°–230° C. The total yield was 94%. 1,3:2,5:4,6-Trimethylenemannitol is reported to melt at 232°–233° C.

Similar results were formed with sulfuric acid and washing the crude product with methanol.

EXAMPLE 5

The two-stage procedure of Example 3 was repeated with mannitol instead of sorbitol to give 10.7 g of the crude white triformal. Elution with methanol left 9.1 g mannitol triformal, mp 230°–231° C. Evaporation of the filtrate and washings left some oily crystals.

The improved process of the invention has several advantages over the processes of the art in terms of shortened reaction times in the order of less than 20 minutes, yields greater than 90%, elimination of solvents, decrease in labor and energy requirements, adaptability to continuous operations, and overall simplicity and convenience. The product, of course, can be used for its conventional purposes which, inter alia, include conversion into ethylenically unsaturated monomers, into aphrogenic and pyrostatic phosphorylated derivatives, and the like. It is further contemplated that many variations can be carried out by the man skilled in the art without departing from the limits of the present invention as claimed.

What is claimed is:

1. A process for the preparation of cyclic formals of polyhydroxy compounds of the formula $CH_2OH(CHOH)_nCH_2OH$ in which n ranges from about 2 to 4, which comprises heating a mixture consisting essentially of such polyhydroxy compound, a slight excess of paraformaldehyde and a catalytic quantity of an acid catalyst to a temperature within the range of about 105° to about 150° C. for a total period of about 10 minutes, such mixture being substantially devoid of water and refluxing agent.

2. The process of claim 1 wherein up to about 1% by weight of water is present in the reaction mixture.

3. The process of claim 1 wherein about 0.1 to 1.0 mole %, based on the polyhydroxy compound, of the acid catalyst is used.

4. The process of claim 1 wherein the polyhydroxy compound is mannitol or sorbitol and the products are the corresponding tricyclic trimethylene compounds.

5. The process of claim 1 wherein the reaction is carried out in two stages, with about one-half to two-thirds of the paraformaldehyde being added in the first stage and heated with the other components for a period about half as long as the total heating time.

6. The process of claim 1 wherein the reaction is carried at a temperature within the range of about 115° to 125° C. for a period of up to 10 minutes.

7. The process of claim 1 wherein the acid catalyst is selected from the group consisting of sulfuric acid, hydrochloric acid, methanesulfonic acid, p-toluenesulfonic acid, boron trifluoride etherate, zinc chloride, aluminum chloride, and mixtures thereof.

* * * * *